United States Patent
Benson

[19]

[11] Patent Number: 6,139,514
[45] Date of Patent: Oct. 31, 2000

[54] FINGER BANDAGE

[76] Inventor: Jacquelyn Benson, 9301 Cottage Park North, Mobile, Ala. 36695

[21] Appl. No.: 09/049,350

[22] Filed: Mar. 27, 1998

[51] Int. Cl.[7] ....................................................... A61F 13/00
[52] U.S. Cl. .................................. 602/63; 602/41; 602/22
[58] Field of Search ................................... 602/44, 41, 63, 602/22

[56] References Cited

U.S. PATENT DOCUMENTS

| | | |
|---|---|---|
| 772,197 | 10/1904 | Weaver . |
| 2,646,797 | 7/1953 | Scholl . |
| 3,306,288 | 2/1967 | Rosenfield . |
| 3,348,541 | 10/1967 | Loebeck . |
| 3,513,842 | 5/1970 | Keenan et al. . |
| 4,858,245 | 8/1989 | Sullivan et al. . |
| 4,926,851 | 5/1990 | Bulley . |
| 5,474,525 | 12/1995 | Blott . |
| 5,499,966 | 3/1996 | Bulley et al. . |
| 5,626,149 | 5/1997 | Schwartz . |

*Primary Examiner*—John G. Weiss
*Assistant Examiner*—Kelvin Hart
*Attorney, Agent, or Firm*—Tipton L. Randall

[57] ABSTRACT

A finger bandage device comprises a tubular member with a closed distal end and an open proximal end. A pad of absorbent material is fastened within the tubular member at the closed distal end. An adhesive material is contained on the inner surface of the proximal end of the tubular member for securing the bandage to a finger inserted therein. Also disclosed is a method of using the bandage for maintaining medication on the fingertip of a wearer, and a method of making the bandage.

4 Claims, 2 Drawing Sheets

FINGER BANDAGE

FIELD OF THE INVENTION

The invention relates to a bandage device, and more particularly, to a specialized bandage for use on a person's finger.

BACKGROUND OF THE INVENTION

Many bandages are commercially available for consumer use. The most common are flat, rectangular adhesive bandage with an absorbent pad positioned at the center of the rectangle. These adhesive bandages function well on relatively flat body parts, but are not suitable for use on rounded body surfaces, particularly on fingertips. The flat bandage, when applied over or around a fingertip, has excess material which protrudes from the finger. The common bandage often presents a slippery outer surface when applied, hindering the use of the finger for operations requiring dexterity, such as typing. The added bulk of the bandage likewise hinders finger dexterity.

Weaver, in U.S. Pat. No. 772,197 discloses a two piece finger cot secured at the edges by an adjustable elastic cord.

In U.S. Pat. No. 2,646,797, Scholl describes a stretchable stocking or bandage made up of an inner layer of foam latex and an outer layer of impervious latex having holes therein.

Rosenfield, in U.S. Pat. No. 3,306,288, discloses a tubular bandage material with elastic threads knitted into the material, causing the bandage to fit snugly over the body part of application.

In U.S. Pat. No. 3,513,842, Keenan et al. describe a protective device for body joints which includes a helical spring in a padded covering.

Bully, in U.S. Pat. No. 4,926,851, discloses a tubular elastic bandage supplied in a length rolled up from opposite ends and used to cover body extremities.

In U.S. Pat. No. 5,626,149, Schwartz describes a medication dispensing sheath for assisting erectile function.

Thus, there is an unmet need for a bandage which securely covers a finger on a person's hand, yet allows the wearer to perform tasks requiring finger dexterity.

SUMMARY OF THE INVENTION

The invention is a bandage for a finger, comprising a tubular member of elastically resilient material with inner and outer surfaces. The tubular member has a closed distal end and an open proximal end. A pad of absorbent material is fastened to the inner surface of the tubular member and positioned at the closed distal end of the tubular member. An adhesive material is contained on at least a portion of the tubular member inner surface near the proximal end thereof, for securing the bandage to a finger inserted into the tubular member. Also disclosed is a method of using the bandage for maintaining medication on the fingertip of a wearer, and a method of making the bandage.

DESCRIPTION OF THE PREFERRED EMBODIMENTS

Definitions

As utilized herein, including the claims, the term "finger" means one of the five digits on the ng the thumb.

As utilized herein, including the claims, the term "distal" means situated away from the point or origin.

As utilized herein, including the claims, the term "proximal" means next to or nearest the point of attachment or origin.

Nomenclature

| 10 | Finger Bandage |
| 12 | Tubular Member |
| 14 | Inner Surface of Tubular Member |
| 16 | Outer Surface of Tubular Member |
| 18 | Closed Distal End of Tubular Member |
| 20 | Open Proximal End of Tubular Member |
| 22 | Pad of Absorbent Material |
| 24 | Adhesive Material |

Construction

As mentioned above, flat bandages do not function well when applied to fingertips. Injuries, including cuts or other trauma, to the fingertips are often encountered in manufacturing as well as in office environments. The finger bandage of the present invention provides protection for the injured fingertip, as well as a means for applying lotion, salve, or medication to the injured area. This bandage fits closely over the injured finger and allows the wearer to maintain a high level of finger dexterity for manual operations, such as typing or light manufacturing tasks.

Figure 1:
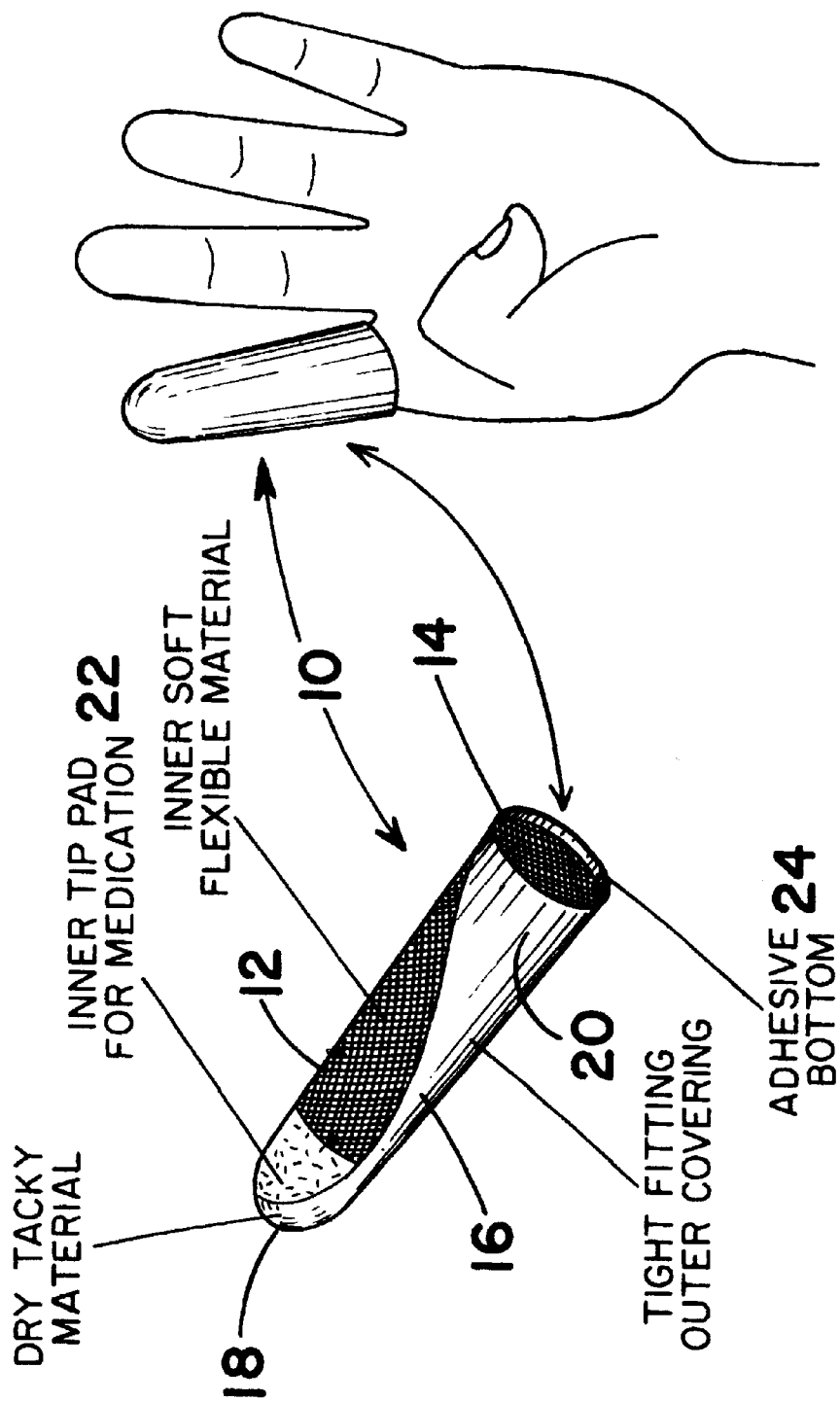
FIG. 1 is a perspective view of the finger bandage of the present invention.
Figure 3:
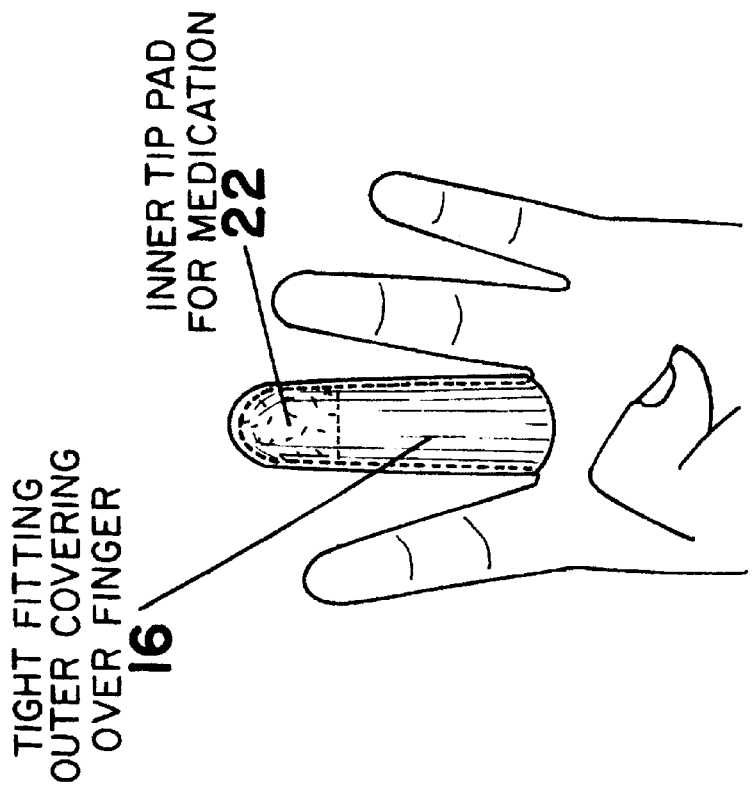
FIG. 3 is a rear view of the bandage applied to a finger on a person's hand.
Figure 2:
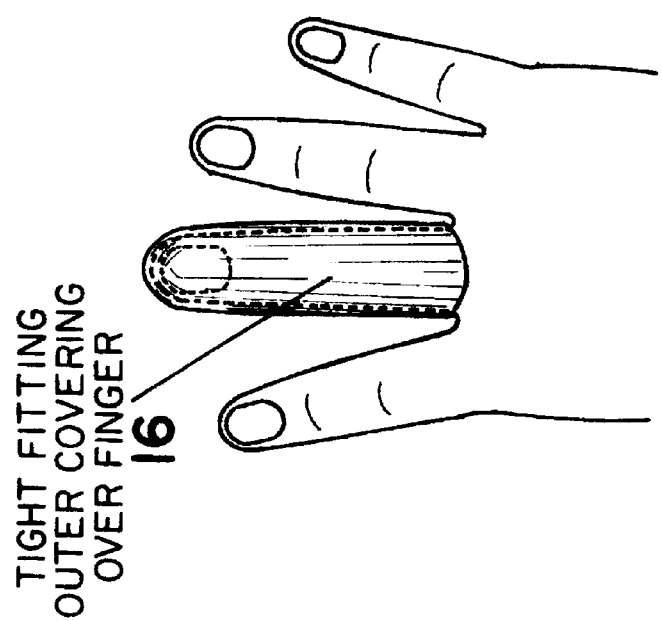
FIG. 2 is a front view of the bandage applied to a finger on a person's hand.

Referring to FIG. 1, the finger bandage of the present invention is shown. This finger bandage 10 comprises a tubular member 12 of elastically resilient material with an inner surface 14 and an outer surface 16. The elastically resilient material may be a woven fabric incorporating elastic threads which allows this material to stretch to some extent to accept a finger inserted into the tubular member 12. The elastically resilient material is available from a number of commercial sources and is well known in the art. The tubular member has a closed distal end 18 and an open proximal end 20 allowing the insertion of a finger therein. A pad of absorbent material 22, such as cotton gauze or some other natural or synthetic material, is fastened to the inner surface 14 of the tubular member 12, near the distal end 18 thereof. The pad of absorbent material 22 conforms to the inner surface 14 of the tubular member 12 and may completely cover the inner distal surface or cover only a selected portion thereof The absorbent pad 22 provides some protection for the injury on the fingertip. However, the principle function of the adsorbent pad 22 is to provide a means of maintaining a protective lotion, salve, or medication in close contact with the injured fingertip. The embodiment of the invention wherein the absorbent pad 22 occupies only a portion of the distal end 18 of the tubular member 12 is shown in FIG. 3. The embodiment of the invention where the absorbent pad 22 occupies the entire distal portion 18 of the tubular member 12 is shown in FIG. 1.

The finger bandage 10 is secured to the finger of the wearer by means of an adhesive material 24 contained on at least a portion of the tubular member inner surface 14 near the proximal end 20 thereof. As shown in FIG. 1, the adhesive material 24 may be present as a continuous band which covers the circumferencial inner surface 14 of the tubular member 12 near the proximal end 20. Alternatively, the adhesive material 24 may be present as intermittent strips on the inner surface 14 of the tubular member 12 near the proximal end 20, The strips may be oriented perpendicular to the opening of the proximal end 20 of the tube member, or at a skewed angle thereto. The surface of the adhesive material 24 is preferably covered with a removable shield material (not shown) which is removed once the finger bandage is positioned on the finger of the wearer, allowing the adhesive material 24 to adhere to the surface of the finger. The removable shield material (not shown) is preferably a thin plastic film with sufficient strength to maintain structural integrity when peeled from the surface of the adhesive material 24.

The finger bandage 10 is shown in a fully unrolled orientation in the Figures. Applying medication, salve or lotion to the absorbent pad member 22 in this orientation may be difficult. It is preferred that the finger bandage 10 be available to the user in an orientation where the proximal open end 20 is rolled outwardly on the outer surface 16 of the tubular member 12. This rolled configuration allows access to the absorbent pad 22 for placement of medication, salve or lotion thereon. In addition, the finger bandage in the rolled configuration can by sealed in a sterile packaging, such as a paper, plastic or foil envelope, to provide additional safety for the user. Upon removal from the packaging, the rolled finger bandage can be placed on the injured finger, unrolled to full extension, and the adhesive material shield removed to secure the bandage in place.

The finger bandage 10 may be sized to fit to the first joint, to the second joint or knuckle, or to the base of the finger. Further, the finger bandage may be manufactured with various internal diameters to accommodate fingers of different sizes. The elastically resilient character of the tubular material allows the encased finger to flex and bend with minimal resistance. The general dry and rough nature of the exterior of the tubular material allows the wearer to perform common tasks requiring a high degree of dexterity.

The present invention includes a method of using the finger bandage to maintain medication on a fingertip. The method of use includes providing a bandage with a tubular member of elastically resilient material, having inner and outer surfaces, and having a closed distal end and an open proxial end. A pad of absorbent material is fastened to the inner surface of the tubular member and positioned at the closed distal end. An adhesive material is contained on at least a portion of the tubular member inner surface near the proximal end. A medication is applied to the pad of absorbent material within the tubular member; and the tubular bandage member is secured upon a finger with the absorbent pad containing applied medication contacting an injured fingertip of the finger.

The present invention also includes a method of making the finger bandage. The method of making includes the steps of forming a tubular member of elastically resilient material, with inner and outer surfaces. The tubular member has a closed distal end and an open proximal end. A pad of absorbent material is fastened to the inner surface of the tubular member, with the pad positioned at the closed distal end. An adhesive material is applied to at least a portion of the tubular member inner surface near the proximal end for securing the bandage to a finger.

While the invention has been particularly shown and described with reference to a preferred embodiment thereof, it will be understood by those skilled in the art that various changes in form and details may be made therein without departing from the spirit and scope of the invention.

What is claimed is:

1. A bandage for a finger comprising;
   a) a flexible tubular member of elastically resilient material, with inner and outer surfaces, having a closed distal end and an open proximal end, said elastically resilient material having a dry and rough outer surface at least at said closed distal end thereof,
   b) a pad of absorbent material fastened only to a portion of the inner surface of said flexible tubular member and positioned at said closed distal end thereof; and
   c) an adhesive material contained on an interior circumference surface of said flexible tubular member inner surface near said proximal end thereof.

2. A bandage according to claim 1 further comprising a removable shield material covering said adhesive material contained on said interior circumference surface of said flexible tubular member inner surface near said proximal end thereof.

3. A method of maintaining medication on a fingertip comprising the steps;
   a) providing a bandage with a flexible tubular member of elastically resilient material, having inner and outer surfaces, having a closed distal end and an open proximal end, said elastically resilient material having a dry and rough outer surface at least at said closed distal end thereof, with a pad of absorbent material fastened only to a portion of the inner surface of said flexible tubular member and positioned at said closed distal end thereof, and an adhesive material contained on an interior circumference surface of said flexible tubular member inner surface near said proximal end thereof;
   b) applying a medication to said pad of absorbent material within said flexible tubular member; and
   c) securing said flexible tubular bandage member upon a finger with said absorbent pad containing applied medication thereon contacting an injured fingertip of the finger.

4. A method of making a finger bandage device comprising;
   a) forming a flexible tubular member of elastically resilient material, with inner and outer surfaces, having a closed distal end and an open proximal end, said elastically resilient material having a dry and rough outer surface at least at said closed distal end thereof;
   b) fastening a pad of absorbent material only to a portion of the inner surface of said flexible tubular member, said pad positioned at said closed distal end thereof; and
   c) applying an adhesive material to an interior circumference surface of said flexible tubular member inner surface near said proximal end thereof for securing the bandage to a finger.

* * * * *